(12) United States Patent
Brewer et al.

(10) Patent No.: US 8,567,401 B2
(45) Date of Patent: Oct. 29, 2013

(54) LOOPED TETHER FOR MEDICAL VENTILATING AND ASPIRATING DEVICES

(75) Inventors: John Brewer, Marietta, GA (US); Cassandra E. Morris, Roswell, GA (US); Ilona F. Weart, Roswell, GA (US)

(73) Assignee: Kimberly Clark Worldwide, Inc., Neenah, WI (US)

( * ) Notice: Subject to any disclaimer, the term of this patent is extended or adjusted under 35 U.S.C. 154(b) by 419 days.

(21) Appl. No.: 12/562,223

(22) Filed: Sep. 18, 2009

(65) Prior Publication Data

US 2011/0067702 A1 Mar. 24, 2011

(51) Int. Cl.
*A61M 16/00* (2006.01)
(52) U.S. Cl.
USPC ............ 128/205.19; 128/202.27; 128/204.18; 128/205.12; 128/205.27; 128/207.14; 128/207.16; 128/912
(58) Field of Classification Search
USPC ............ 128/202.27, 204.18, 205.12, 205.19, 128/205.24, 205.27, 207.14, 207.16, 912; 600/156; 604/19
See application file for complete search history.

(56) References Cited

U.S. PATENT DOCUMENTS

| | | | | |
|---|---|---|---|---|
| 2,908,522 A | * | 10/1959 | Glave | 292/288 |
| 4,045,058 A | * | 8/1977 | Eross | 285/119 |
| 5,357,952 A | * | 10/1994 | Schuster et al. | 128/207.17 |
| 5,806,816 A | * | 9/1998 | Hull et al. | 248/205.6 |
| 5,826,599 A | * | 10/1998 | Adams | 132/308 |
| 6,408,850 B1 | | 6/2002 | Sudge | |
| 7,188,623 B2 | * | 3/2007 | Anderson et al. | 128/207.16 |
| 2005/0131446 A1 | | 6/2005 | Coughlin et al. | |
| 2006/0005841 A1 | | 1/2006 | Anderson et al. | |

FOREIGN PATENT DOCUMENTS

| | | |
|---|---|---|
| EP | 0 366 478 A2 | 5/1990 |
| EP | 0 559 977 A1 | 9/1993 |
| EP | 0 692 273 A1 | 1/1996 |
| WO | WO 93/21981 A2 | 11/1993 |
| WO | WO 96/09082 A1 | 3/1996 |
| WO | WO 2006/014431 A2 | 2/2006 |
| WO | WO 2007/142801 A1 | 12/2007 |
| WO | WO 2007/143502 A2 | 12/2007 |

* cited by examiner

*Primary Examiner* — Clinton T Ostrup
(74) *Attorney, Agent, or Firm* — James B. Robinson

(57) ABSTRACT

There is provided a looped tether to prevent the over-withdrawal of a suction catheter from a connecting fitting in a closed suction catheter respiratory device. The looped tether is made from a single thread or strand that is looped or doubled in length with the two loose ends connected together to produce the loop. The looped tether provides better distribution of the forces at the ends of the device and is relatively simple to assemble. Also provided is a system for preventing the over-withdrawal of a suction catheter from a connecting fitting in a closed suction catheter respiratory device.

7 Claims, 4 Drawing Sheets

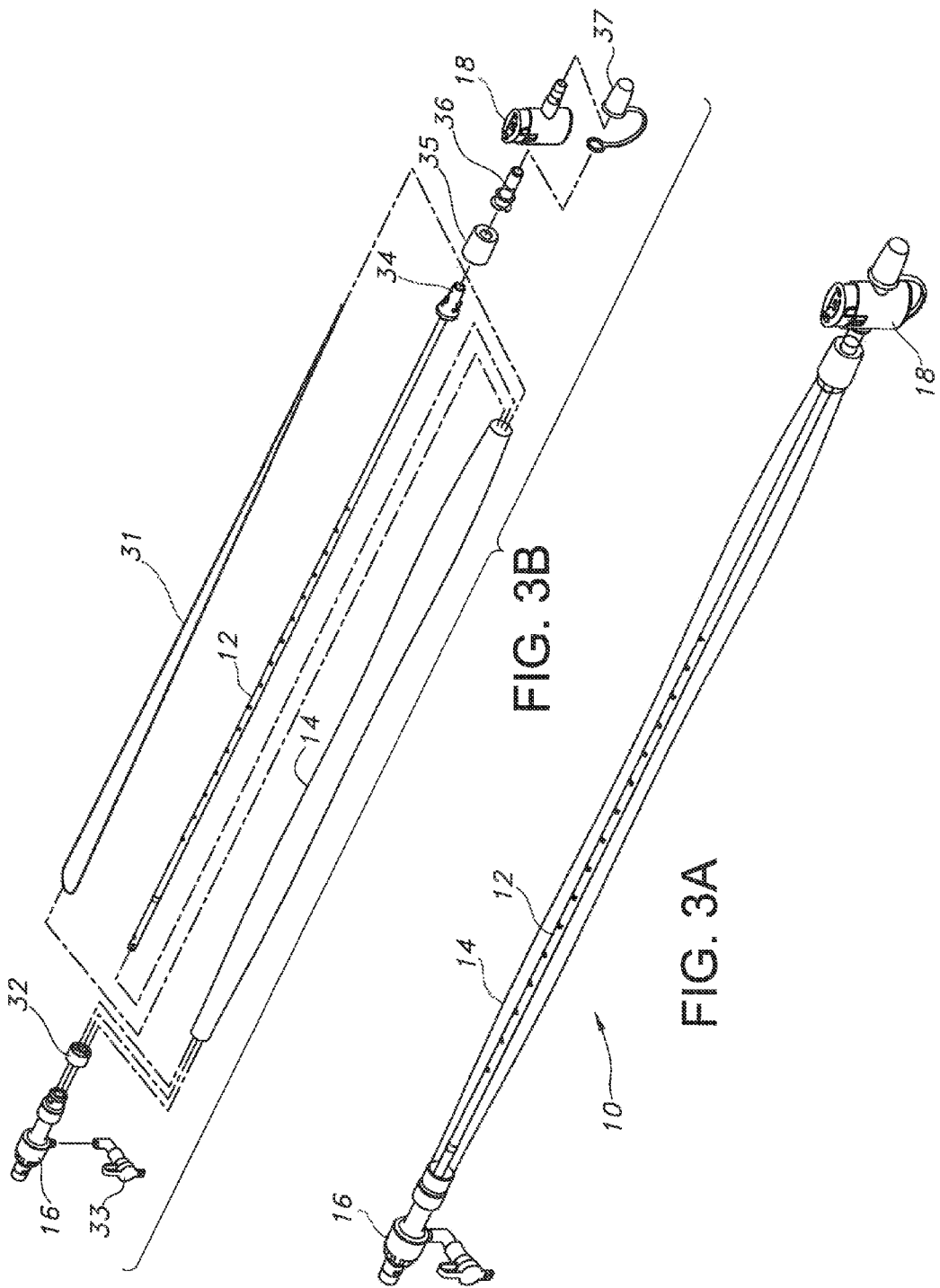

LOOPED TETHER FOR MEDICAL VENTILATING AND ASPIRATING DEVICES

BACKGROUND

Tracheal catheters are used to assist patient breathing during and after medical procedures until they are able to breathe successfully on their own and be removed from assisted breathing. One type of tracheal catheter, the endotracheal tube (ET tube), is inserted through the mouth of a patient and guided past the vocal cords and glottis into the trachea. Once the patient is intubated, the ET tube is connected to ventilators or respirators for mechanical ventilation of the lungs. Another type of tracheal catheter, the tracheostomy tube (trach tube), is inserted through a stoma in the throat, directly into the trachea and may also be connected to a ventilator. The ventilator unit is connected to a hose set; the ventilation tubing or tubing circuit, delivering the ventilation gas to the patient as a ventilating system.

Removing secretions from the trachea-bronchial tree is an integral part of the care given to patients who are intubated and receiving mechanical or other artificial ventilation. Secretions can be excessive in some respiratory disorders and constitute a serious threat to the patient having such respiratory disorders. The presence of a tracheal catheter is a hindrance to the patient's efforts to clear secretions through natural coughing. In current medical practice, suction catheters are inserted into the lungs to clear such secretions from the patient's airway by suctioning.

Suctioning may be performed using an "open" or "closed" system. In the open system, the suction catheter is merely a flexible plastic tube that is inserted into the tracheal catheter ventilating lumen with a source of suction connected to the proximal end of the suction catheter. The suction catheter is advanced as far as desired and suction is applied to remove secretions. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device 10 which may be used to suction secretions uses a suction catheter 12 enclosed within a generally cylindrical plastic sleeve 14 to eliminate or minimize contamination of the suction catheter prior to use (FIG. 1). This is generally referred to as a "closed suction catheter" and may be available under the trade names TRACH CARE® from BALLARD® Medical Products and KIMVENT®, all from Kimberly-Clark Corporation. As the patient requires artificial removal of secretions, the suction catheter 12 may be advanced through one end of the plastic sleeve 14, through a connecting fitting 16, into the tracheal catheter and, if desired, into one of the main bronchi of the patient. The other, proximal end 17 of the suction catheter 12 is attached to a source of suction 19. Suction is applied to the proximal end 17 of the suction catheter 12 using a finger controlled valve 18 to remove the secretions. The other bronchus may likewise be aspirated. Secretions are thus drawn into the lumen of the suction catheter 12 and removed and the system remains closed. The suction catheter 12 is subsequently withdrawn from the tracheal catheter and back into the plastic sleeve 14 to keep the circuit closed. Closed suction systems are generally preferred by healthcare providers since the medical care provider is better protected from the patient's secretions. Closed suction systems are also easier and quicker to use since a sterile field need not be created each time the patient must be suctioned, as is required in open suction systems.

One drawback to the closed suction catheter system described above has been the over-withdrawal of the suction catheter 12 into the plastic sleeve 14. If a user pulls the suction catheter too much, the suction catheter 12 can slip out of the proximal end of the connecting fitting 16. When this occurs the seal between the suction catheter 12 and the connecting fitting 16 is lost and pressurized air from the ventilator enters the plastic sleeve 14, expanding it and possible rupturing it. A failure of the plastic sleeve 14 can expose the medical personnel in the area to the airborne secretions of the patient. Such a failure can also reduce ventilator efficiency for the patient, leading to patient complications and even death.

In order to prevent the suction catheter from pulling out of the connecting fitting, various "stops" have been proposed. Making the distal end of the suction catheter too large to fit through the connecting fitting, for example, has been investigated but not adopted since a strong caregiver may still be able to over-withdraw the suction catheter and in so doing, break off a piece of the suction catheter that could fall into the respiratory tract of a patient.

U.S. Pat. Nos. 5,598,840 and 5,088,486 contain a cursory reference to a single lanyard, cord or tether running between the two ends of the plastic sleeve. Neither reference, however, explains how such a tether may be installed or attached or what it should be made from. U.S. Pat. No. 7,188,623 describes press-fitting two parts of each end of a closed suction catheter together and placing between the press-fit parts a single, preferably monofilament tether, thus placing the tether in a pinch hold to resist the force exerted by an attempted over-withdrawal. Unfortunately, it has been quite surprisingly found that using press-fit parts to hold a tether is insufficient. The average health care provider can easily apply enough force to pull an end of the tether from the pinch of the press-fitted parts and this requires no more than ordinary strength. Another surprise found was the degree to which monofilament stretches with the application of moderate force, making such a material unsuited for this use.

Lastly, in manufacturing terms, the cutting of a length of cord and attaching it to each end of a closed suction catheter results in the addition of the tolerances allowed at each connection. This adding of manufacturing tolerances, sometimes referred to in the art as "stack up", can result in the suction catheter tip being some distance from the correct position when it is in the withdrawn position, even if each individual component of the system is within its manufacturing tolerances.

It would be desirable to have a system for prohibiting the over-withdrawal of the suction catheter from the connecting fitting without the drawbacks of the prior art techniques, that distributes the forces more evenly and that is relatively simple and cost effective to produce.

SUMMARY

There is provided a tether to prevent the over-withdrawal of a suction catheter from a connecting fitting in a closed suction catheter respiratory device. The tether is in the form of a loop and runs from a first end of the device to a second end and back within a sleeve. The looped tether provides better distribution of the forces at the ends of the device so that is does not pull out of position or damage the device. The looped tether has the added benefit of being relatively simple to assemble. Also provided is a system for preventing the over-withdrawal of a suction catheter from a connecting fitting in a closed suction catheter respiratory device.

BRIEF DESCRIPTION OF THE DRAWINGS

FIG. 3A shows a closed suction catheter with a looped tether and FIG. 3B shows that same device in an exploded view.

DETAILED DESCRIPTION

Reference is now made to the drawings wherein like numerals are used to designate like parts throughout.

Figure 1:
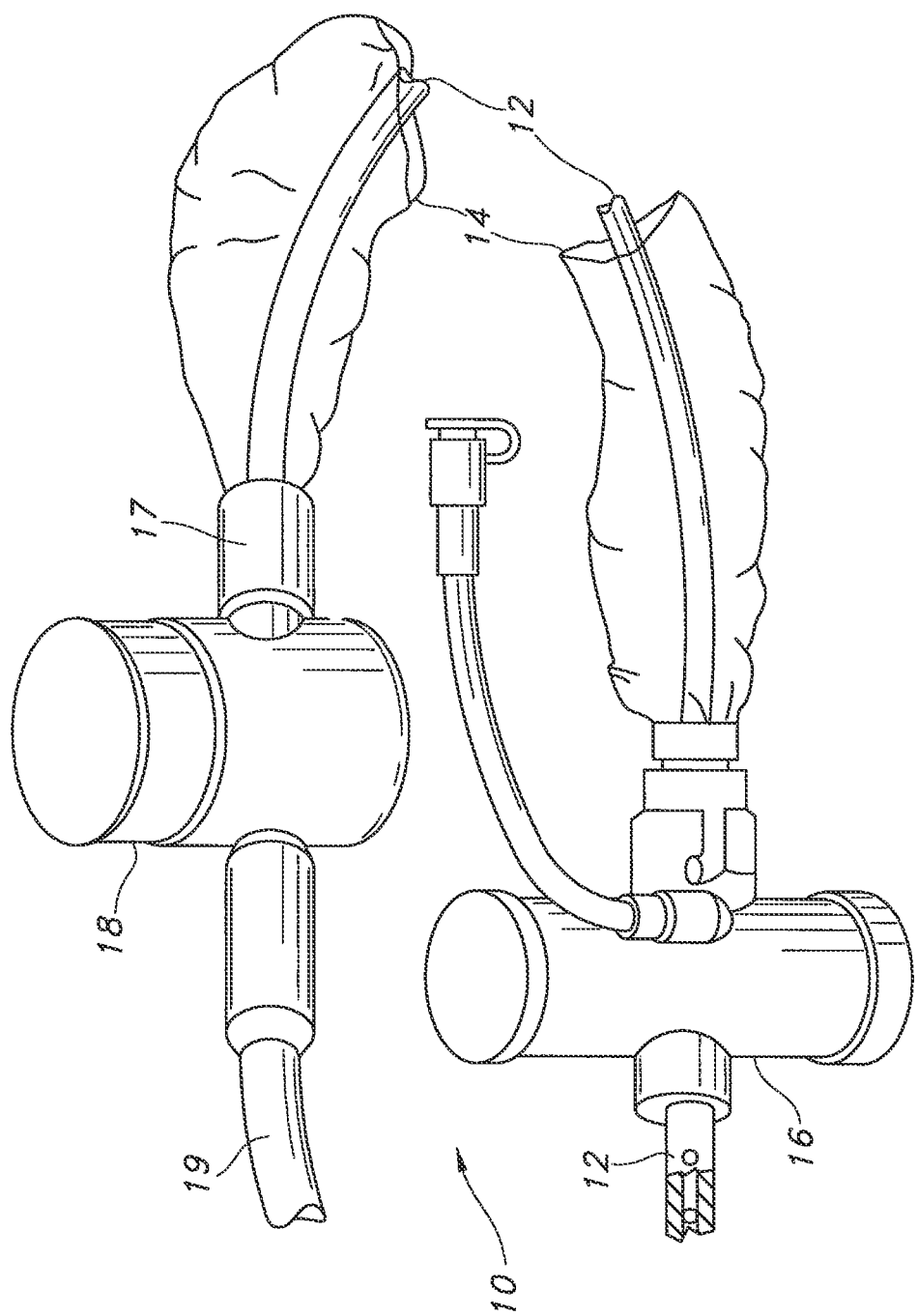
FIG. 1 shows a device which may be used to clear secretions from the lungs of a patient as described in U.S. Pat. No. 4,569,344.

FIG. 1 illustrates an aspirating/ventilating apparatus disclosed U.S. Pat. No. 4,569,344, also referred to under the trade name TRACH CARE® or KIMVENT®. This closed suction catheter aspirating device 10 is attached to the patient's tracheal catheter using a fitting 16 and may be included as part of an overall ventilation circuit. The suction catheter 12 is enclosed within a plastic sleeve 14 to eliminate or minimize contamination of the catheter. As the patient requires artificial removal of secretions, the suction catheter is advanced through the distal fitting 16 of the ventilating device into the tracheal catheter (not shown), into the patient's airway and then into one of the lungs of the patient. Suction is applied using a finger controlled suction valve 18 on the proximal end of the catheter 12 to remove the secretions. A more detailed description of this care device may be found in U.S. Pat. No. 4,569,344.

Figure 2:
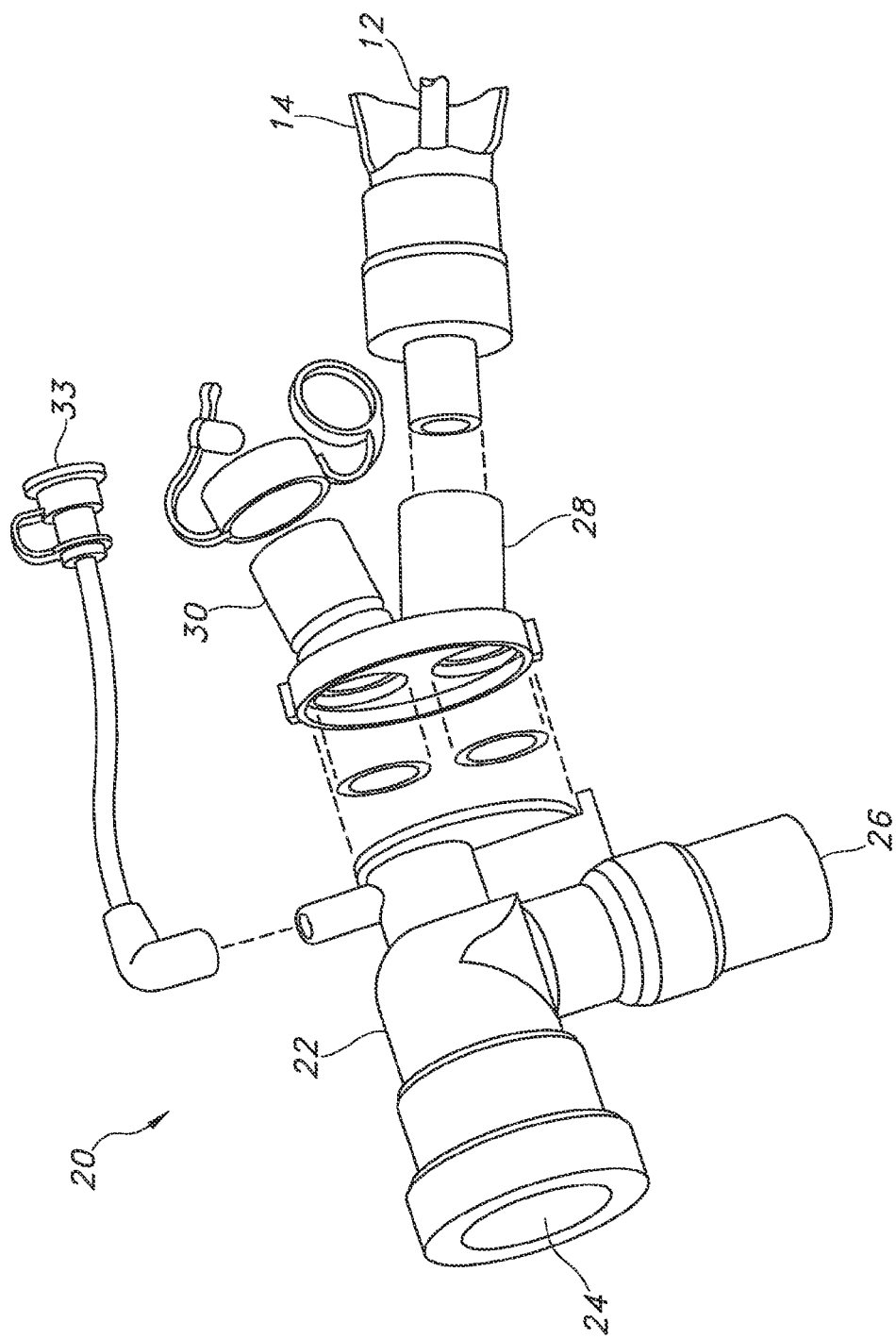
FIG. 2 shows a multiple-access manifold mounted as described in U.S. Pat. No. 5,735,271 which may be placed between the tracheal care device of U.S. Pat. No. 4,569,344 and the ventilation circuit.

The closed suction aspirating device 10 of FIG. 1 may be used by attaching it directly to a tracheal catheter or in other configurations as long as it may move in a substantially straight alignment into the tracheal catheter. One of the ways the aspirating device 10 may be used is to attach it to a multiple-access manifold 20 like, for example, that shown in U.S. Pat. No. 5,735,271 (FIG. 2). The multiple-access manifold 20 has a rotating mechanism so that a user may choose which port is aligned with the tracheal catheter. As shown in FIG. 2, the manifold assembly accommodates continual cyclic patient ventilation, independent of implementation by the health care provider of any other patient respiratory access procedure. Access port 33 accommodates introduction of irrigation or wash liquid by which the exterior of an aspirating or suction catheter 12, for example, is washed as the catheter 12 is withdrawn following use. The distal end 24 of the device is connected to a tracheal catheter (not shown) through which the patient is ventilated. The access port 26 may be connected to the ventilator and ports 28 and 30 may accommodate accessory devices. One device may be the aspirating or suction catheter 12, for example, as shown adjacent to the port 28. The other port 30 may be used with the port seal as described in the Summary. When it is desired to use the aspirating device, the manifold may be rotated so that the catheter aligns with the distal port 24. The catheter 12 may be then advanced through the manifold and into the bronchial tube of the patient and suction may be applied as described previously. A more detailed description of this device may be found in U.S. Pat. No. 5,735,271.

FIG. 3A is a drawing of an exemplary closed suction catheter device 10. The catheter 12 is contained within the sleeve 14. On the patient or distal end is the distal fitting 16 and on the proximal end is the suction controlling valve 18. FIG. 3B shows an exploded view of the exemplary closed suction catheter device 10. The catheter 12, sleeve 14 and looped tether 31 are clearly visible.

In one embodiment, in order to produce the looped tether, an appropriate length of cord is cut and the ends tied together with a knot 42. This process may be performed by machine so that there is little to no variation in the length of the final looped tether 31. This provides an advantage over a single pass tether since this process has only one manufacturing tolerance control point; the loop length. A single pass tether has two manufacturing tolerance points; where it is attached to each end of the catheter. It can be appreciated by those skilled in the art of manufacturing processes that this assembly system lends itself to very consistent catheter length control.

Figure 5A:
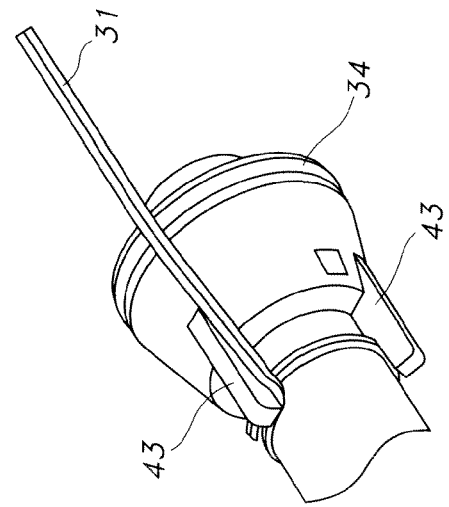
FIGS. 5A and 5B show two views of the looped tether knot retainer end of the suction catheter.
Figure 5B:
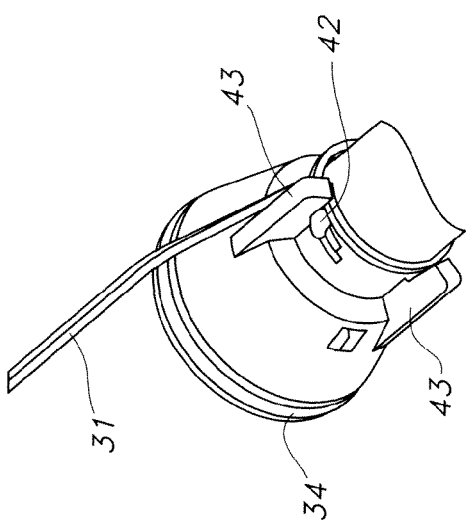

On a first or proximal end of the catheter 12, the looped tether knot 42 is slipped under at least one knot stay 43 on the proximal fitting 34, which holds the knot 42 in place (FIGS. 5A and 5B). There are desirably three knot stays 43, so that the looped tether 31 may be wrapped around the proximal fitting 34 and slipped under the plurality of knot stays 43. It is preferred that the looped tether 31 is wrapped around the fitting 34 one time and that the strands then change direction and travel towards the distal end side by side as shown in FIG. 5B. This results in a more secure attachment of the looped tether 31 to the proximal end, probably due to a better distribution of forces around the fitting 34. It has been surprisingly found that without the desired wrapping of the looped tether around the fitting 34, the knot itself can move or "roll" down the line towards the line ends and eventually become untied, resulting in failure of the looped tether. In an alternative embodiment, the looped tether may be wrapped around the fitting 34 one time as described above, with the strands then changing direction on separate stays 43 so that the strands are not side by side as they travel towards the distal end of the catheter.

Figure 4A:
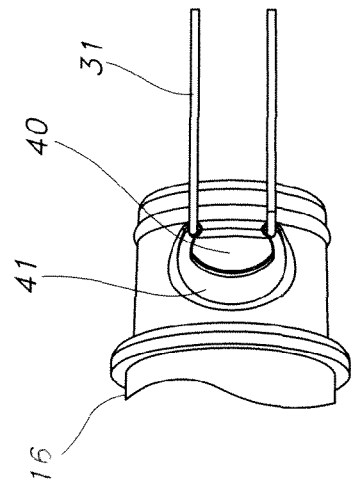
FIGS. 4A and 4B show two views of the looped tether loop retainer end of the suction catheter.
Figure 4B:
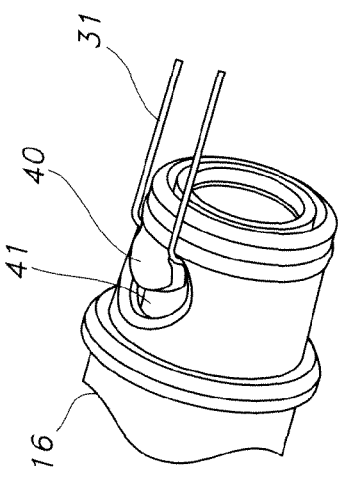

On a second or distal end of the catheter 12, the loop of the looped tether 31 is hooked over at least one loop tab 40 formed in a cleft 41 on the proximal end of the distal fitting 16 (FIGS. 4A and 4B). This can be accomplished very simply using manual labor. There may be more than one loop tab 40 on the distal fitting on, for example opposite sides of the fitting and the looped tether 31 may be hooked over more than one loop tab 40 if desired. This may help distribute tensile forces around the fitting.

The looped tether 31 need not be placed on the loop tab 40 at exactly the halfway point of the loop since the looped tether 31 is not firmly attached at this point and may slide around the loop tab 40. This provides a manufacturing advantage as the loop may "self-center" when the proximal and distal fittings are moved away from each other as assembly continues, i.e. via tension. A further advantage provided by the looped tether passing around the loop tab 40 over that of a single length tether is that the looped tether distributes the forces on two sides of the tab. It was found that a single tether, attached to a tab, would result in the tether actually cutting into the corner of the tab due to the extreme force exerted when an attempted over-withdrawal of the catheter occurs. A tab made from the same material but using a loop that contacts the tab at two points as shown in the FIG. 4B, does not suffer from this phenomenon, again probably due to a better distribution of forces.

Once the looped tether 31 is attached to both fittings 16, 34 and centered on the loop tab 40, assembly continues by inserting the catheter 12 into the center hole or passageway of the distal fitting 16, slipping the sleeve 14 over the catheter 12, looped tether 31 and distal fitting 16 and press fitting the distal collar 32 over the distal fitting 16. The press fitted distal collar 32 squeezes the sleeve 14 and looped tether 31 so that the sleeve 14 is sealed and so that the looped tether 31 does not slip off the loop tab 40. In a similar manner to the assembly of the distal end, the proximal end components may be held together by a press-fitted proximal collar 35 that holds the sleeve 14 and looped tether 31 in place by pressing tightly against the proximal fitting 34, holding the sleeve 14 and looped tether 31 between the fitting 34 and proximal collar 35 so that the knot does not slip out of the knot stay 43. This press-fitting process merely holds the looped tether on the knot stay and the loop tab at their respective ends, it does not create a pinch hold that resists the force exerted when an attempted over-withdrawal occurs. The use of adhesive may be avoided using this method so that the attachment of the tether at both ends of the catheter is essentially free of any adhesive.

The looped tether may be made from any "low elongation" material that has sufficient tensile strength for this purpose, i.e. those from which a thread with an elongation of 1 percent or less at a tensile force load of 10 pounds. (4.5 kilograms) may be made. The looped tether is made from thread that is formed from multiple strands or filaments that may be braided or twisted. The thread should have a failure (breaking) tensile strength of at least 5 pounds (2.3 kg), more desirably at least 10 pounds and still more desirably at least 25 pounds. These include metals like low carbon steels and aluminum, and plastics like polyvinyl alcohol, polyester, polyamide including aromatic polyamide (aramid), polyolefins like polyethylene and polypropylene and cellulose like cotton, flax, jute and others. Suitable commercially available polymeric materials are sold under the names KEVLR®, TWARON®, TECHNORA®, SPECTRA® and VECTRAN®.

SPECTRA® fiber is a very high molecular density form of polyethylene available from Honeywell International Inc and others. The gel-spinning manufacturing process aligns the molecules, which vastly increases the strength of the material. It is twice as strong as hardened steel (per unit area) but one-tenth the density, and is lighter than water. One thread suitable for use as the looped tether is SPECTRA® fiber 4 ply thread sold under the designation Tex-92, having a Z twist and a proprietary soft sizing finish and available from Gudebrod Inc. of Pottstown, Pa. This thread uses 4 fibers that are individually twisted, plied and given a final twist and heat bonding of 8 to 10 percent bond area with a coating of Lubrizol PERFORMAX® coating. Tex-92 has a tensile strength of 56 to 58 pounds (25 to 26 kg) with an elongation of 3.5 to 4 percent at that load.

The looped tether loop is desirably formed from a length of cord that is doubled and connected to itself near its ends. This end where the cord is connected to itself is referred to herein as the "knot end", though use of this term is not meant to limit the invention. Suitable connecting methods include any of the following: knots, sleeves, grips, clips, splices and over molded anchors. The looped tether is secured to the suction valve end and the patient end so that the greatest span between them is half the circumference of the loop less those cord portions directly in contact with the fitting components.

For illustrative purposes only, securing the looped tether loop to the proximal and distal connector components may be accomplished with the knot end secured to the former and the loop portion farthest from the knot end secured to the latter; the reverse arrangement is equally feasible to construct. To secure the loop tether, the knot end lodges in a catch or stay 43 on the proximal fitting 34 while the rest of the loop passes between the main body of the fitting 34 and the stay 43, encircles a distal portion of the proximal fitting 34 and passes between the fitting 34 and the stay 43 again (FIGS. 5A and 5B). This encirclement by the part of the looped tether immediately adjacent the knot distributes securing forces radially on the suction control valve end's proximal fitting 34 to help ensure the knot end remains lodged in the stay 43.

In addition, it may be desirable for certain applications to use a loop tab 40 on both ends of the suction catheter and forgo the use of a knot in a stay 43 at one end or conversely, to use a knot in a stay 43 at both ends of the suction catheter and forgo the use of a loop tab 40, by forming a loop tether from two separate cords tied together with a knot on each end. Suction catheters with looped tethers attached using loop tabs on both end or using knots in stays at both ends are intended to be within the scope of this disclosure.

To further secure the knot end and the encircling portion of the loop in the stay 43 and against the distal portion of the proximal fitting 34, a first tubular retainer member or proximal collar 35 is pressure fit over and frictionally engages the distal end of the proximal fitting 34. Also between this collar 35 and the distal end of the suction control proximal fitting 34 and directly contacting the secured loop portions that have been wrapped around the fitting 34 is one end of a collapsible plastic bag or sleeve 14. The remaining unsecured portion of the loop is located within the balance of the sleeve and the farthest loop portion from the knot end is available for subsequent securing to the distal fitting 16.

The distal fitting 16 has a proximal portion that contains a cleft 41 and a loop tab 40 to accommodate and secure a portion of the loop. The farthest portion of the loop from the knot end is inserted and lodged into the cleft so that tension forces applied on the loop are at least distributed to two corners of the cleft 41 at the base of the loop tab 40. Optionally, the cleft can be formed to have smooth rounded indentations at the corners to further lodge the loop within them and to have the outer facing edge of the cleft rounded to facilitate insertion of the loop into the cleft.

To further secure the loop in the cleft a second tubular retaining member or distal collar 32 is pressure fitted over and frictionally against the proximal end of the distal fitting 16. Between this second collar 32 and the proximal end of the distal fitting 16 and directly contacting loop portions that extend out of the cleft is the other end of the collapsible sleeve 14.

Modifications and variations of the presently disclosed device will be obvious to those of skill in the art from the foregoing detailed description. Such modifications and variations are intended to come within the scope of the following claims.

We claim:

1. A closed suction catheter device having two ends and comprising a continuous looped tether connected to the two ends of the device, wherein said looped tether runs from a first end of the device to a second end and back within a sleeve, wherein said looped tether has an elongation of less than 1 percent at a tensile load of 10 pounds, wherein said continuous looped tether is formed with a connection to itself and the connection is lodged under a stay on the first end of the device, the tether then wrapped around the first end and under the stay, and wherein said looped tether is loosely connected to said second end by slipping the loop over at least one loop tab, thereby allowing the tether to self-center on the tab on the second end as the two ends are moved apart during assembly.

2. The device of claim 1 wherein said continuous looped tether forms a connection to itself by a method or device selected from the group consisting of knots, sleeves, grips, clips, splices, twists and over molded anchors.

3. The device of claim 1 whereas the attachment of the tether to said first and second ends of said catheter is essentially free of adhesive.

4. The device of claim 1 wherein said looped tether is made from a polymer selected from the group consisting of cellulose, polyamides, polyolefins, polyvinyl alcohols, polyesters and combinations thereof.

5. The device of claim 1 wherein the looped tether is at least one fiber, twisted or braided.

6. The device of claim 5 wherein said looped tether is coated to improve strength and frictional force distribution.

7. The device of claim 1 wherein said looped tether has a tensile strength of at least 5 pounds.

\* \* \* \* \*